(12) United States Patent
Meepowpan et al.

(10) Patent No.: US 9,637,507 B2
(45) Date of Patent: May 2, 2017

(54) PROCESS FOR THE PREPARATION OF LIQUID TIN(II) ALKOXIDES

(71) Applicant: CHIANG MAI UNIVERSITY, Mueang Chiang Mai (TH)

(72) Inventors: Puttinan Meepowpan, Mueang Chiang Mai (TH); Winita Punyodom, Mueang Chiang Mai (TH); Robert Molloy, Mueang Chiang Mai (TH)

(73) Assignee: CHIANG MAI UNIVERSITY, Mueang Chiang Mai (TH)

( * ) Notice: Subject to any disclaimer, the term of this patent is extended or adjusted under 35 U.S.C. 154(b) by 38 days.

(21) Appl. No.: 14/442,672

(22) PCT Filed: Oct. 30, 2013

(86) PCT No.: PCT/TH2013/000061
§ 371 (c)(1),
(2) Date: May 13, 2015

(87) PCT Pub. No.: WO2014/077785
PCT Pub. Date: May 22, 2014

(65) Prior Publication Data
US 2016/0280726 A1   Sep. 29, 2016

(30) Foreign Application Priority Data
Nov. 14, 2012 (TH) .................... 1201006169

(51) Int. Cl.
*C07K 7/00* (2006.01)
*C07F 7/22* (2006.01)

(52) U.S. Cl.
CPC .......... *C07F 7/2232* (2013.01); *C07F 7/2296* (2013.01)

(58) Field of Classification Search
CPC ........................................ C07F 7/22
USPC ............................................. 556/81
See application file for complete search history.

(56) References Cited

U.S. PATENT DOCUMENTS

| 6,414,174 B1 | 7/2002 | Boyle |
| 2012/0214959 A1 | 8/2012 | Lee et al. |

OTHER PUBLICATIONS

Kleawkla et al., Advanced Materials Research (2008), 55-57, 757-760.*
Morrison et al., J. Inorg. Nucl. Chem., 1967. vol. 29, pp. 393-400.*
Kleawkla et al., Advanced Materials Res. 2008, 55-57, 757-760.*
International Search Report mailed on Jan. 30, 2014 for PCT/TH2013/000061 filed on Oct. 30, 2013 in the name of Chiang Mai University.
Written Opinion mailed on Jan. 30, 2014 for PCT/TH2013/000061 filed on Oct. 30, 2013 in the name of Chiang Mai University.
International Preliminary Report on Patentability for PCT Application No. PCT/TH2012/000061 filed Oct. 30, 2013 on behalf of Chiang Mai University. Mailed May 19, 2015.
Hans R. Kricheldorf, et al. "Polylactones: 31. Sn(II)octoate-initiated polymerization of L-lactide: a mechanistic study". Polymer 1995, 36, 1253-1259.
Hans R. Kricheldorf et al. "Polylactones 48. SnOct2-Initiated Polymerizations of Lactide: A Mechanistic Study". Macromolecules 2000, 33, 702-709.
Adam Kowalski et al. "Kinetics and mechanism of cyclic esters polymerization initiated with tin(II) octoate, 1". Macromol Rapid Commun. 1998, 19, 567-572.
Adam Kowalski et al. "Mechanism of Cyclic Ester Polymerization Initiated with Tin(II) Octoate. 2. Macromolecules Fitted with Tin(II) Alkoxide Species Observed Directly in MALDI-TOF Spectra". Macromolecules 2000, 33, 689-695.
Adam Kowalski et al. "Kinetics and Mechanism of Cyclic Esters Polymerization Initiated with Tin (II) Octoate. 3. Polymerization of L, L-Dilactide". Macromolecules 2000, 33, 7359-7370.
Eberhard Amberger et al. "Methoxide des Zinns" Chem. Ber. 1963, 96, 2562-2565.
James S. Morrison et al. "Some Reactions of Tin (II) Chloride in Nonaqueous Solution". J Inorg. Nucl. Chem. 1967, 29, 393-400.
Ray Gsell et al. "Synthesis and Spectroscopic Properties of Tin (II) Alkoxides". J Jnorg. Nucl. Chem. 1975, 37, 1133-1137.

* cited by examiner

*Primary Examiner* — Sudhakar Katakam
*Assistant Examiner* — Kofi Adzamli
(74) *Attorney, Agent, or Firm* — Steinfl + Bruno LLP

(57) ABSTRACT

A synthetic process of producing liquid tin(II) alkoxides for use as either catalysts in the synthesis of lactide or as initiators in the polymerization of cyclic ester monomers to yield biodegradable polyesters is described. The synthetic process employs anhydrous tin(II) chloride dissolved in n-heptane mixed with dry diethylamine. Alcohols, ROH, in which the R groups are n-$C_4H_9$, n-$C_6H_{13}$, and n-$C_8H_{17}$ are added to the reaction mixture and stirred for 12 hours. The reaction mixture is then filtered under nitrogen or argon before being evaporated to dryness to yield the three tin(II) alkoxides, namely: tin(II) n-butoxide, tin(II) n-hexoxide, and tin(II) n-octoxide. All three tin(II) alkoxides are viscous, dark yellow liquids which are highly soluble in most common organic solvents. Furthermore, they can all be stored under an inert atmosphere for long periods without any significant change in their reactivity and, therefore, in their effectiveness as catalysts/initiators.

6 Claims, 2 Drawing Sheets

(A) Sn(OnC4H9)2    (B) Sn(OnC6H13)2    (C) Sn(OnC8H17)2

PROCESS FOR THE PREPARATION OF LIQUID TIN(II) ALKOXIDES

CROSS REFERENCE TO RELATED APPLICATIONS

The present application is the US national stage of International Patent Application PCT/TH2013/000061 filed internationally on Oct. 30, 2013 which, in turn, claims priority to Thai Patent Application No. 1201006169 filed on Nov. 14, 2012.

FIELD OF THE INVENTION

This invention is pertaining to organic chemistry focusing on the preparation and spectroscopic characterization of novel liquid tin(II) alkoxides.

BACKGROUND OF THE INVENTION

Recently, the uses of poly(l-lactide), poly(d-lactide), poly (dl-lactide), poly($\epsilon$-caprolactone), polyglycolide, and other high molecular weight copolymers in the production of biodegradable containers have increased dramatically due to concerns regarding non-degradable petrochemical products which cause severe environmental problems.

Generally, the synthesis of high molecular weight polyester requires ring-opening polymerization (ROP) of a cyclic ester monomer using tin(II) octoate ($Sn(Oct)_2$) and an alcohol as the initiating system. There are two proposed mechanisms in this well-known process as suggested by 1) Kricheldorf and co-workers [Hans R. Kricheldorf, I. Kreiser-Saunders, and Caroline Boettcher, *Polymer* 1995, 36, 1253-1259, and Hans R. Kricheldorf, Ingrid Kreiser-Saunders, and Andrea Stricker, *Macromolecules* 2000, 33, 702-709] and 2) Penczek and co-workers [Adam Kowalski, Andrzej Duda, and Stanislaw Penczek, *Macromol. Rapid Commun.* 1998, 19, 567-572; Adam Kowalski, Andrzej Duda, and Stanislaw Penczek, *Macromolecules* 2000, 33, 689-695, and Adam Kowalski, Andrzej Duda, and Stanislaw Penczek, *Macromolecules* 2000, 33, 7359-7370]. Kricheldorf proposed the coordination of $Sn(Oct)_2$ and the alcohol with the initial cyclic ester following by ring-opening polymerization. The former serves as a reagent whereas the latter is an initiator, as depicted in the following chemical equation:

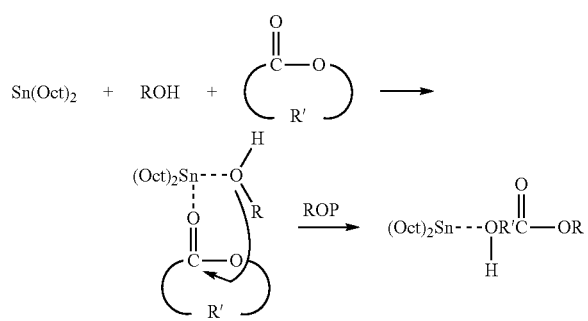

In contrast, Penczek suggested the reaction between $Sn(Oct)_2$ and the alcohol, resulting in the formation of $Sn(Oct)(OR)$ and $Sn(OR)_2$, the true initiators of this reaction as shown in the following chemical equations:

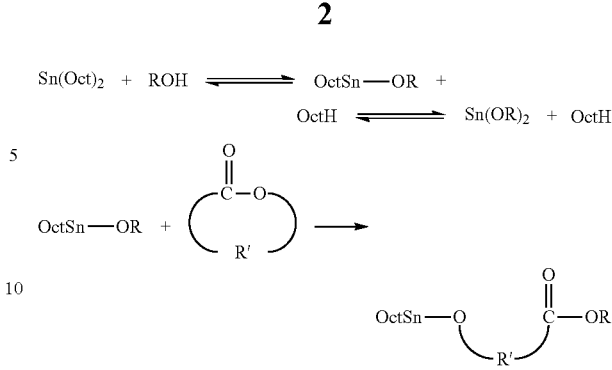

The latter mechanism has been widely accepted as the most reasonable mechanistic pathway. To produce high molecular weight polyesters via ring-opening polymerization, it is extremely important to know the exact concentration of the tin(II) alkoxide initiator which should be highly soluble in the cyclic ester monomer. For these reasons, our research group has been focusing on liquid tin(II) alkoxide derivatives which are soluble in common organic solvents and cyclic ester monomers.

Tin(II) alkoxides were firstly prepared by Amberger and Kula [Eberhard Amberger, Maria-Regina Kula, *Chem. Ber.* 1963, 96, 2562-2565] in 1963, using anhydrous tin(II) chloride to react with sodium methoxide ($NaOCH_3$) in methanol as shown in the following equation:

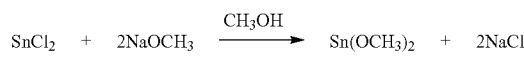

White, hygroscopic solid tin(II) methoxide ($Sn(OCH_3)_2$) was obtained from this preparation. Later in 1967, Morrison and Haendler [James S. Morrison and Helmut M. Haendler, *J. Inorg. Nucl. Chem.* 1967, 29, 393-400] developed a more convenient synthetic method using tin(II) chloride dihydrate ($SnCl_2 \cdot 2H_2O$, 6.0 g, 0.032 mol), dried with acetic anhydride (($CH_3CO)_2O$). Dry tin(II) chloride was dissolved in anhydrous methanol (anh. $CH_3OH$, 200 mL), under a nitrogen atmosphere. A solution of triethylamine ($Et_3N$) was added slowly until the precipitation was complete. The resulting solution was filtered, washed several times with methanol to remove triethylamine hydrochloride and then washed with diethyl ether. The product was subsequently dried under reduced pressure. The overall chemical equation for this preparation may be represented as:

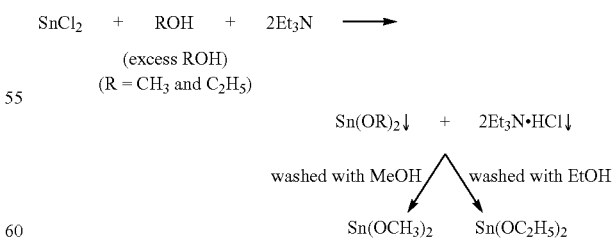

Tin(II) ethoxide ($Sn(OCH_2CH_3)_2$) can be synthesized in a similar fashion. Tin(II) chloride dihydrate (3.0 g, 0.015 mol) was dissolved in anhydrous ethanol ($CH_3CH_2OH$, 75 mL). The white solid obtained turned yellow rapidly, even when the product was dried and kept under vacuum. Solubility tests showed that both tin(II) methoxide and tin(II) ethoxide dissolved only slightly in several organic solvents.

In 1975, Gsell and Zeldin [Ray Gsell and Martel Zeldin, *J. Inorg. Nucl. Chem.* 1975, 37, 1133-1137] prepared tin(II) n-butoxide ($Sn(OnC_4H_9)_2$) via transesterification of tin(II) methoxide. Tin(II) methoxide was refluxed with excess n-butanol ($n$-$C_4H_9OH$) in toluene ($C_6H_5CH_3$) until the solution became clear and colorless. Toluene and n-butanol were removed until the volume of solution was about 100 mL. The solution was cooled to room temperature and crystalline tin(II) n-butoxide was obtained, as shown in the following equation:

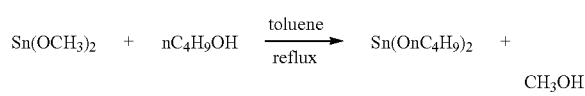

The tin(II) n-butoxide product was a white solid with a melting point of 171-172° C. and was extremely moisture and oxygen sensitive. As the alkyl chain became longer, such as in changing from $CH_3$ to $C_2H_5$, the solubility of the product in organic solvents increased slightly. The physical and chemical properties relating to tin(II) methoxide, tin(II) ethoxide and tin(II) n-butoxide are summarized in Table 1, while their $^1$H-NMR spectroscopic data are shown in Table 2.

TABLE 1

Molecular formulae, physical appearances, melting points and solubilities of solid tin(II) alkoxides synthesized by Gsell and Zeldin.

| Tin(II) alkoxide | Molecular formula | Physical appearance | m.p. (° C.)/Solubility |
|---|---|---|---|
| Tin(II) methoxide | $Sn(OCH_3)_2$ | White solid | 242-243° C./slightly dissolves in organic solvents at room temperature but hardly dissolves in polar solvents at high temperature |
| Tin(II) ethoxide | $Sn(OC_2H_5)_2$ | White solid | Decomposes at T >200° C. before the melting point/insoluble in most organic solvents at room temperature but dissolves in polar solvents such as o-dichlorobenzene at high temperature |
| Tin(II) n-butoxide | $Sn(O\text{—}n\text{-}C_4H_9)_2$ | White solid | 171-172° C./partially soluble in organic solvents |

TABLE 2

$^1$H-NMR data (220 MHz) of solid tin(II) alkoxides synthesized by Gsell and Zeldin.

| Tin(II) alkoxide | Solvent | Temp (° C.) | Chemical shift (δ, ppm) |
|---|---|---|---|
| Tin(II) methoxide | o-$C_6H_4Cl_2$ | 75 | 6.5 (s, br) |
| | o-$C_6H_4Cl_2$ | 150 | 6.48 (s) |
| Tin(II) ethoxide* | o-$C_6H_4Cl_2$ | 35 | 1.17 (t), 1.23 (t), 3.80 (q), 3.99 (q) |
| | o-$C_6H_4Cl_2$ | 150 | 1.20 (t), 3.85 (q)† |
| Tin(II) n-butoxide*,‡,# | $C_6H_6$ | 35 | 0.85 (t)‡, 1.30 (h, γ), 1.65 (q, β), 3.80 (t, α) |
| | o-$C_6H_4Cl_2$ | 100 | 0.96 (t, δ)‡, 1.45 (h, γ), 1.72 (q, β), 4.09 (t, α) |

TABLE 2-continued $^1$H-NMR data (220 MHz) of solid tin(II) alkoxides synthesized by Gsell and Zeldin.

| Tin(II) alkoxide | Solvent | Temp (° C.) | Chemical shift (δ, ppm) |
|---|---|---|---|
| | | | (spectrum shown in the following figure) |

Note:
*J = 7 Hz
†The ratio of t/q = 1.5
‡Recorded on NMR 220 MHz
Proton positions of $CH_3$—$CH_2$—$CH_2$—$CH_2$— are α, γ, β, and δ, respectively In accordance with the U.S. Pat. No. 6,414,174 B1 (Jul. 2, 2002), Boyle and co-workers reported the preparation of a tin complex from the hydrolysis of tin(II) tert-butyl-methoxide in the presence of a basic reagent. ($Sn(N(CH_3)_2)_2)_2$ was dissolved in hexane and two mole equivalence of tert-butylmethanol ($(CH_3)_3CCH_2OH$) were added. The reaction mixture was stirred for 24 hours and then warmed for an additional 1 hour. All solvents were removed in vacuo and the product washed with hexane and recrystallized from hot tetrahydrofuran (THF). Tin(II) tert-butylmethoxide was obtained as a white solid in its polymeric form of $((Sn(OCH_2C(CH_3)_3)_2)_2)_n$, which barely dissolved in tetrahydrofuran. Later, Boyle and co-workers carried out the hydrolysis of $(Sn(OCH_2C(CH_3)_3)_2)_n$ using water in the amounts of 0.50-0.75 and 0.30-0.50 mole equivalence relative to the starting material. The results showed that tin(II) tert-butylmethoxide was obtained in the forms of $Sn_6(O)_4(OCH_2C(CH_3)_3)_4$ and $Sn_5(O)_2(OCH_2C(CH_3)_3)_6$, respectively.

The major drawback of these tin(II) compounds, such as tin(II) alkoxide ($Sn(OR)_2$) where R=$CH_3$, $C_2H_5$, and $n$-$C_4H_9$, as reported by Morrison and Haendler, and Gsell and co-workers, is their poor solubility in common organic solvents in the temperature range of 25-35° C. Solubility increases in highly polar solvents and at higher temperatures. Moreover, tin(II) alkoxides synthesized by Morrison and Haendler's procedure using several alcohols such as $CH_3OH$, $C_2H_5OH$, $n$-$C_3H_7OH$, $n$-$C_4H_9OH$, $n$-$C_6H_{13}OH$, and $n$-$C_8H_{17}OH$, are all white solids. Solubility test results for these tin(II) alkoxides in general organic solvents are summarized in Table 3. All of the tin(II) alkoxides are insoluble in all ten non-polar aprotic solvents but are slightly soluble in polar solvents when heated.

TABLE 3

Solubility test results of tin(II) alkoxides in normal organic solvents.

| Tin(II) alkoxide | Chloroform/ toluene/ n-heptane | Methanol/ acetone/ tetrahy-drofuran | Dimethyl sulfoxide/ o-dichlorobenzene |
|---|---|---|---|
| $Sn(OCH_3)_2$ (solid) | x | x | x |
| $Sn(OC_2H_5)_2$ (solid) | x | x | x |
| $Sn(O\text{—}n\text{-}C_3H_7)_2$ (solid) | x | x | o |
| $Sn(O\text{—}n\text{-}C_4H_9)_2$ (solid) | x | x | o |
| $Sn(O\text{—}n\text{-}C_6H_{13})_2$ (solid) | x | x | o |
| $Sn(O\text{—}n\text{-}C_8H_{17})_2$ (solid) | x | x | o |

Note:
Solid tin(II) alkoxides were synthesized by the method reported by Morrison and Haendler.
x is insoluble even when heat was applied
o is slightly soluble upon heating
✓ is completely soluble in the temperature range of 25-35° C.

The inventors have tried to synthesize tin(II) alkoxides with R groups of $n\text{-}C_4H_9$, $n\text{-}C_6H_{13}$ and $n\text{-}C_8H_{17}$ using the procedure reported by Gsell and Zeldin but no liquid tin(II) alkoxides could be obtained due to the tendency for self-aggregation of the tin(II) alkoxide molecules, as illustrated in the following figure:

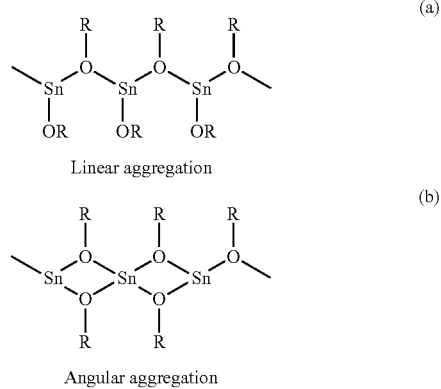

(a) Linear aggregation (b) Angular aggregation

The self-aggregation of tin(II) alkoxide molecules makes them insoluble and also inhibits their transesterification with the desired alcohols. Additionally, solid tin(II) alkoxides synthesized by the procedure reported by Morrison and Haendler contain significant amounts of triethylamine hydrochloride. This requires large quantities of alcohol to remove the salt by-product in the washing step, producing unnecessary and unwanted alcohol waste. Only moderate percent yields (~50%) were obtained after the washing step. Due to their low solubility in most organic solvents and cyclic ester monomers, the polymerizations of monomers such as l-lactide, d-lactide, dl-lactide, ε-caprolactone and other cyclic esters are relatively slow and ineffective. Furthermore, it is difficult to effectively control the molecular weight of the final polymer product which is also contaminated with some residual solid tin(II) alkoxide initiator.

SUMMARY OF THE INVENTION

The main advantage of the liquid tin(II) alkoxides prepared in this invention is that they are soluble in general organic solvents by 1) using anhydrous tin(II) chloride instead of tin(II) chloride dehydrate, 2) using diethylamine as a base or ligand in the 2.0-2.1 mole equivalence of anhydrous tin(II) chloride and 3) using n-heptane, which is a non-polar aprotic solvent. N-heptane can solvate the molecules of tin(II) alkoxide produced from the reaction and prevent both self-aggregation of the tin(II) alkoxide and aggregation of bridging alcohols with tin(II) alkoxide molecules. Aggregation is the major cause of the relative poor solubility of tin(II) alkoxides in normal organic solvents and cyclic ester monomers.

The primary objective of this synthetic process of liquid tin(II) alkoxides is to prepare a suitable reagent/initiator for the synthesis of l-lactide, d-lactide, dl-lactide, polylactide, poly-(ε-caprolactone), polyglycolide, and other co-polyesters. Liquid tin(II) alkoxides can be homogeneously dissolved or mixed with many monomers such as lactide, ε-caprolactone, glycolide and other cyclic esters during the melting process. When these tin(II) alkoxides are used as initiators in polymerization, it is possible to control the molecular weight of the polymer formed and also obtain high molecular weights. These advantages can be applied to the production of biodegradable polyesters for use in both biomedical and environmental applications.

BRIEF DESCRIPTION OF DRAWINGS

For a fuller understanding of the invention, reference is made to the following description, taken in connection with the accompanying drawings, in which.

DETAILED DESCRIPTION OF THE PREFERRED EMBODIMENTS

Figure 1:
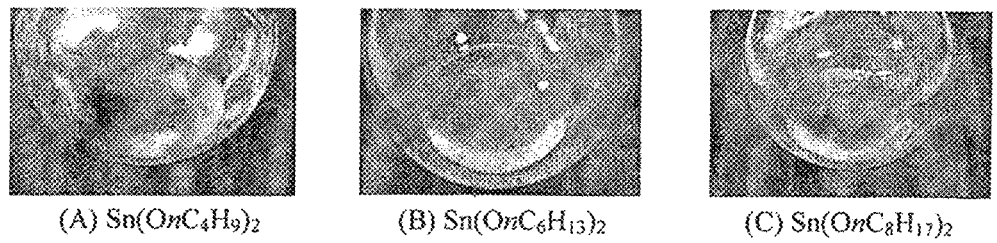
FIG. 1 shows the physical appearances of liquid tin(II) alkoxides: (A) tin(II) n-butoxide, (B) tin(II) n-hexoxide, and (C) tin(II) n-octoxide

This invention describes the development of the synthetic process of liquid tin(II) alkoxides which are soluble in organic solvents for the preparation of lactide and polyesters by using anhydrous tin(II) chloride instead of tin(II) chloride dehydrate, 2) changing from triethylamine to diethylamine or other amines such as dimethylamine, diisopropylamine, and trimethyl-amine as a base or ligand to enhance the nucleophilicity on the substitution of chlorine atoms, resulting in the formation of $SnCl_2 \cdot HNEt_2$ in high yield, as shown in the following equation:

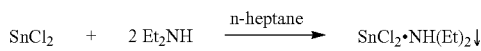

This also allows the alcohol to react with the tin atom of $SnCl_2 \cdot HNEt_2$ better than that of $SnCl_2 \cdot NEt_3$. Finally, 3) by using one of the following nonpolar aprotic solvents: n-heptane, n-hexane, cyclohexane, benzene, toluene, xylene, and tetrahydrofuran instead of an excess of a polar, protic solvent such as an alcohol., the nonpolar aprotic solvent molecules can surround the molecules of tin(II) alkoxide, thereby preventing their self-aggregation. If excess alcohol is used, it can result in the formation of tin(II) alkoxide with bridging alcohol molecules leading to the poor solubility of tin(II) alkoxide in most common organic solvents. Moreover, the use of nonpolar aprotic solvents causes the precipitation of $Et_2NH.HCl$ from the soluble tin(II) alkoxide so that purification of tin(II) alkoxide prior to use is not necessary.

The objective of the synthetic process of liquid tin(II) alkoxides is to obtain products which can act as reagents in the synthesis of lactides such as l-lactide, d-lactide, and dl-lactide and as initiators in the synthesis of polyesters from cyclic esters such as polylactide, poly-($\epsilon$-caprolactone), polyglycolide, and co-polyesters. This procedure is the first successful process to produce liquid tin(II) alkoxides with no such procedure having yet been reported in the literature. All three tin(II) alkoxides: tin(II) n-butoxide ($Sn(O-n-C_4H_9)_2$), tin(II) n-hexoxide ($Sn(O-n-C_6H_{13})_2$), and tin(II) n-octoxide ($Sn(O-n-C_8H_{17})_2$), which were synthesized from this process, are viscous, dark yellow liquids. They could be mixtures of monomer, dimer, trimer, and/or oligomers that are still soluble in common organic solvents in the temperature range of 25-38° C. They can be stored under a nitrogen or argon atmosphere without any significant effect on their reactivity. Moreover, the products from this process do not require any further purification and can be used either as a reagent or initiator in the solution phase.

The synthetic process of liquid tin(II) alkoxides in this invention is composed of several important steps which are 1) the use of anhydrous tin(II) chloride instead of tin(II) chloride dihydrate, 2) the use of dimethylamine, diisopropylamine, trimethylamine or triethylamine in the 2.0-2.1 mole equivalence of anhydrous tin(II) chloride to enhance the nucleophilicity or ligand ability in the substitutions of chloride compared to the use of triethylamine, resulting in the formation of $SnCl_2.HNEt_2$ in high yield and giving a better reaction between the alcohol molecule and the tin atom of $SnCl_2.HNEt_2$ than that of $SnCl_2.NEt_3$, and most importantly, 3) the use of one of the suggested nonpolar aprotic solvents such as n-heptane, n-hexane, cyclohexane, benzene, toluene, xylene, and tetrahydrofuran instead of polar protic solvents such as alcohols to inhibit the formation of tin(II) alkoxide self-aggregates. Moreover, nonpolar aprotic solvent also allow for the precipitation and therefore easy separation of $Et_2NH.HCl$ from the tin(II) alkoxide in solution. Thus, no further purification of tin(II) alkoxide is required; 4) the amount of alcohol used in this process is about 2.0-2.1 mole equivalence of the anhydrous tin(II) chloride to reduce the aggregation of tin(II) alkoxide in the presence of excess alcohol.

Examples 1 for chemicals used in process for the preparation of liquid tin(II) alkoxides ($Sn(OR)_2$) are:

1. Anhydrous tin(II) chloride, purity >98%, purchased from Aldrich. Molecular weight=189.62 g/mol, boiling point=652° C., and melting point=246° C.

2. Diethylamine (($C_2H_5$)NH). Molecular weight=73.14 g/mol, boiling point=55° C., melting point=−50° C., density=0.707 g/mL (25° C.). Must be purified by refluxing with sodium (Na) or calcium hydride ($CaH_2$) for 1 hour and distilled prior to use. Dry diethylamine is kept under nitrogen or argon, or kept in a container with molecular sieves.

3. N-butanol (n-$C_4H_9OH$). Molecular weight=74.12 g/mol, boiling point=116-118° C., melting point=−90° C., density=0.81 g/mL (25° C.). Must be purified by refluxing with sodium (Na) for 1 hour and distilled prior to use. Dry n-butanol is kept under nitrogen or argon, or kept in a container with molecular sieves.

4. N-hexanol (n-$C_6H_{13}OH$). Molecular weight=102.17 g/mol, boiling point=156-157° C., melting point=−52° C., density=0.814 g/mL (25° C.). Must be purified by refluxing with sodium (Na) for 1 hour and distilled prior to use. Dry n-hexanol is kept under nitrogen or argon, or kept in a container with molecular sieves.

5. N-octanol (n-$C_8H_{17}OH$). Molecular weight=130.23 g/mol, boiling point=196° C., melting point=−15° C., density=0.827 g/mL (25° C.). Must be purified by refluxing with sodium (Na) for 1 hour and distilled prior to use. Dry n-octanol is kept under nitrogen or argon, or kept in a container with molecular sieve.

6. N-heptane (n-$C_7H_{16}$). Molecular weight=100.20 g/mol, boiling point=98° C., melting point=−91° C., density=0.684 g/mL (25° C.). Must be purified by refluxing with sodium (Na) for 1 hour and distilled prior to use. Dry n-heptane is kept under nitrogen or argon, or kept in a container with molecular sieves.

To fully understand this invention, the following further details are given:

Example 2 for the preparation of liquid tin(II) n-butoxide ($Sn(O-n-C_4H_9)_2$)

1. A three-necked round bottom flask is equipped with a magnetic bar, an oven-dried gas-inlet, and a dropping funnel. It is placed on a magnetic stirrer. A gas-inlet is connected to a volumetric gauge-controlled nitrogen or argon source via a plastic tube.

2. Anhydrous tin(II) chloride 4.84 g (25.01 mmol) is added to the reaction flask.

3. Dry n-heptane (ca. 100 mL) is added into the reaction vessel at the temperature range of 25-38° C. The mixture was well-stirred for 30-60 minutes.

4. Dry diethylamine (5.43 mL, 52.53 mmol) is then added into the reaction vessel in the temperature range of 15-20° C. The reaction mixture is stirred for 3-6 hours.

5. Solution of dry n-butanol 4.81 mL (52.53 mmol) in dry n-heptane (ca. 50 mL) was added to the reaction mixture in the temperature range of 25-38° C. The resulting solution is stirred for another 12 hours.

6. The reaction mixture is filtered under nitrogen or argon, and the solid residue is thoroughly washed with dry n-heptane (100-200 mL).

7. The filtrate is concentrated and evaporated to dryness on a rotary evaporator.

8. The residue of tin(II) n-butoxide is further dried using a high vacuum pump for another 3-6 hours.

9. Tin(II) n-butoxide is obtained as viscous, dark yellow liquid, in 4.89 g, 73.79% yield.

Example 3 for the preparation of liquid tin(II) n-hexoxide ($Sn(O-n-C_6H_{13})_2$)

1. A three-necked round bottom flask is equipped with a magnetic bar, an oven-dried gas-inlet, and a dropping funnel. It is placed on a magnetic stirrer. A gas-inlet is connected to a volumetric gauge-controlled nitrogen or argon source via a plastic tube.

2. Anhydrous tin(II) chloride 4.84 g (25.01 mmol) is added to the reaction flask.

3. Dry n-heptane (ca. 100 mL) is added into the reaction vessel at the temperature range of 25-38° C. The mixture was well-stirred for 30-60 minutes.

4. Dry diethylamine (5.43 mL, 52.53 mmol) is then added into the reaction vessel in the temperature range of 15-20° C. The reaction mixture is stirred for 3-6 hours.

5. Solution of dry n-hexanol 6.59 mL (52.53 mmol) in dry n-heptane (ca. 50 mL) was added to the reaction mixture in the temperature range of 25-38° C. The resulting solution is stirred for another 12 hours.

6. The reaction mixture is filtered under nitrogen or argon, and the solid residue is thoroughly washed with dry n-heptane (100-200 mL).

7. The filtrate is concentrated and evaporated to dryness on a rotary evaporator.

8. The residue of tin(II) n-hexoxide is further dried using a high vacuum pump for another 3-6 hours.

9. Tin(II) n-hexoxide is obtained as viscous, dark yellow liquid, in 6.97 g, 86.73% yield.

Example 4 for the preparation of liquid tin(II) n-octoxide $(Sn(O-n-C_8H_{17})_2)$ 1. A three-necked round bottom flask is equipped with a magnetic bar, an oven-dried gas-inlet, and a dropping funnel. It is placed on a magnetic stirrer. A gas-inlet is connected to a volumetric gauge-controlled nitrogen or argon source via a plastic tube.

2. Anhydrous tin(II) chloride 4.84 g (25.01 mmol) is added to the reaction flask.

3. Dry n-heptane (ca. 100 mL) is added into the reaction vessel at the temperature range of 25-38° C. The mixture was well-stirred for 30-60 minutes.

4. Dry diethylamine (5.43 mL, 52.53 mmol) is then added into the reaction vessel in the temperature range of 15-20° C. The reaction mixture is stirred for 3-6 hours.

5. Solution of dry n-octanol 8.27 mL (52.53 mmol) in dry n-heptane (ca. 50 mL) was added to the reaction mixture in the temperature range of 25-38° C. The resulting solution is stirred for another 12 hours.

6. The reaction mixture is filtered under nitrogen or argon, and the solid residue is thoroughly washed with dry n-heptane (100-200 mL).

7. The filtrate is concentrated and evaporated to dryness on a rotary evaporator.

8. The residue of tin(II) n-octoxide is further dried using a high vacuum pump for another 3-6 hours.

9. Tin(II) n-octoxide is obtained as viscous, dark yellow liquid, in 7.00 g, 74.18% yield.

Products from the syntheses of liquid tin(II) alkoxides, their molecular formula, physical appearances, percentage yields and solubilities are summarized in FIG. 1 and Table 4-5.

TABLE 4

Molecular formula, physical appearances, and percentage yields of tin(II) alkoxides.

| Tin(II) alkoxide | Molecular formula | Physical appearances | Percent yield |
|---|---|---|---|
| Tin(II) n-butoxide | $Sn(O-n-C_4H_9)_2$ | Viscous, dark yellow liquid | 73.79 |
| Tin(II) n-hexoxide | $Sn(O-n-C_6H_{13})_2$ | Viscous, dark yellow liquid | 86.73 |
| Tin(II) n-octoxide | $Sn(O-n-C_8H_{17})_2$ | Viscous, dark yellow liquid | 74.18 |

TABLE 5

Solubilities of liquid tin(II) alkoxides in various organic solvents.

| Tin(II) alkoxide | Chloroform/ toluene/ n-heptane | Methanol/ acetone/ tetrahydrofuran | Dimethyl sulfoxide/ o-dichlorobenzene |
|---|---|---|---|
| Tin(II) n-butoxide | ✓ | x | x |
| Tin(II) n-hexoxide | ✓ | x | x |
| Tin(II) n-octoxide | ✓ | x | x |

Note:
x is insoluble even when heated.
✓ is soluble at room temperature.

Figure 2:
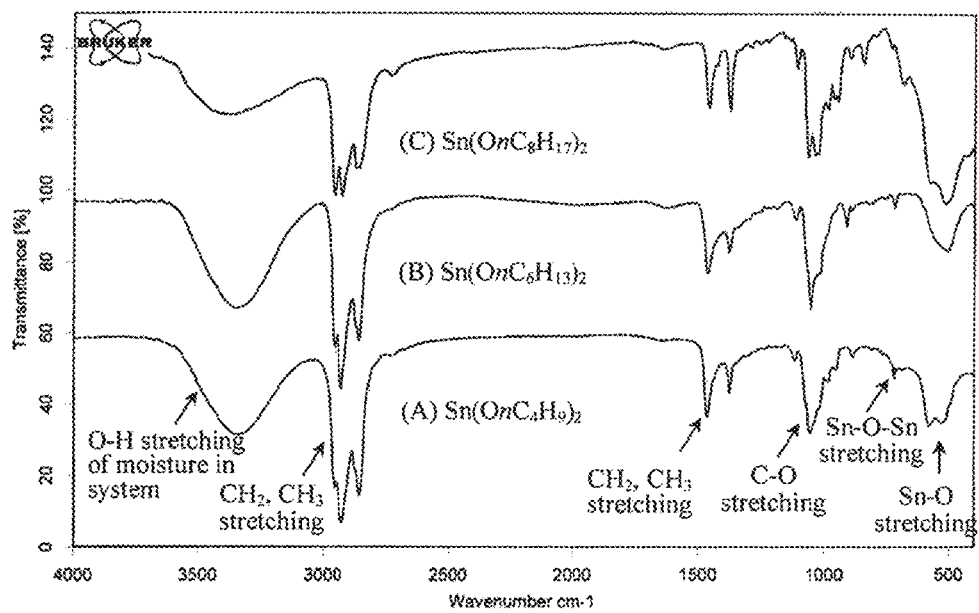
FIG. 2 shows the IR spectra (neat) of liquid tin(II) alkoxides: (A) tin(II) n-butoxide, (B) tin(II) n-hexoxide, and (C) tin(II) n-octoxide

IR characterization data of the liquid tin(II) alkoxides synthesized as described in the invention compared with that of solid tin(II) alkoxides are shown in FIG. 2 and Table 6.

TABLE 6

IR characterization data of liquid tin(II) alkoxides and their respective solid forms.

| | Wavenumber (v, cm$^{-1}$) | | | | | |
|---|---|---|---|---|---|---|
| | $Sn(O-n-C_4H_9)_2$ | | $Sn(O-n-C_6H_{13})_2$ | | $Sn(O-n-C_8H_{17})_2$ | |
| Assignment | Solid* | Liquid | Solid* | Liquid | Solid* | Liquid |
| CH$_3$ | 2911 (w) | 2956 (s) | 2911 (w) | 2950 (s) | 2911 (w) | 2953 (s) |
| | | 2862 (s) | | | | |
| CH$_2$ | | 2922 (s) | | 2925 (s) | | 2922 (s) |
| | | 2851 (s) | | 2858 (s) | | 2851 (s) |
| CH$_3$ (def) | | 1369 (m) | 1377 (w) | 1378 (m) | 1377 (w) | 1373 (m) |
| CH$_2$ (def) | | 1455 (m) | | 1455 (m) | | 1455 (m) |
| C—O (stretch) | 1014 (w) | 1067 (m) | 1007 (w) | 1052 (m) | 1007 (w) | 1049 (m) |
| | | 1039 (m) | | 1025 (m) | | 1014 (m) |
| Sn—O—Sn (stretch) | | 740 (w) | | 740 (w) | | 740 (w) |
| Sn—O (stretch) | 541 (s) | 573 (br s) | 541 (s) | 505 (br m) | 541 (s) | 581 (br m) |
| | | 512 (br s) | | | | 528 (br m) |

Note:
*Solid tin(II) alkoxides were synthesized by the method reported by Morrison and Haendler.
def = deformation;
s = strong;
m = medium;
br = broad;
w = weak Molecular weights of liquid tin(II) alkoxide analyzed by GC-MS and LC-MS techniques are tabulated in Table 7.

TABLE 7

Molecular ions of liquid tin(II) alkoxides from GC-MS and LC-MS techniques.

| Tin(II) alkoxide | Found molecular ion (m/z) | Structure of found molecular ion |
|---|---|---|
| $Sn(O-n-C_4H_9)_2$ | 264[†] | $M^+ = [Sn(OnC_4H_9)_2]^+$ |
| (MW = 264) | 265[‡] | $[M + H]^+ = [Sn(OnC_4H_9)_2 + H]^+$ |
|  | 287[‡] | $[M + Na]^+ = [Sn(OnC_4H_9)_2 + Na]^+$ |
| $Sn(O-n-C_6H_{13})_2$ | 320[†] | $M^+ = [Sn(OnC_6H_{13})_2]^+$ |
| (MW = 320) | 321[‡] | $[M + H]^+ = [Sn(OnC_6H_{13})_2 + H]^+$ |
|  | 343[‡‡] | $[M + Na]^+ = [Sn(OnC_6H_{13})_2 + Na]^+$ |
| $Sn(O-n-C_8H_{17})_2$ | 376[†] | $M^+ = [Sn(OnC_8H_{19})_2]^+$ |
| (MW = 376) | 377[‡] | $[M + H]^+ = [Sn(OnC_8H_{19})_2 + H]^+$ |
|  | 399[‡] | $[M + Na]^+ = [Sn(OnC_8H_{19})_2 + Na]^+$ |

Figure 3:
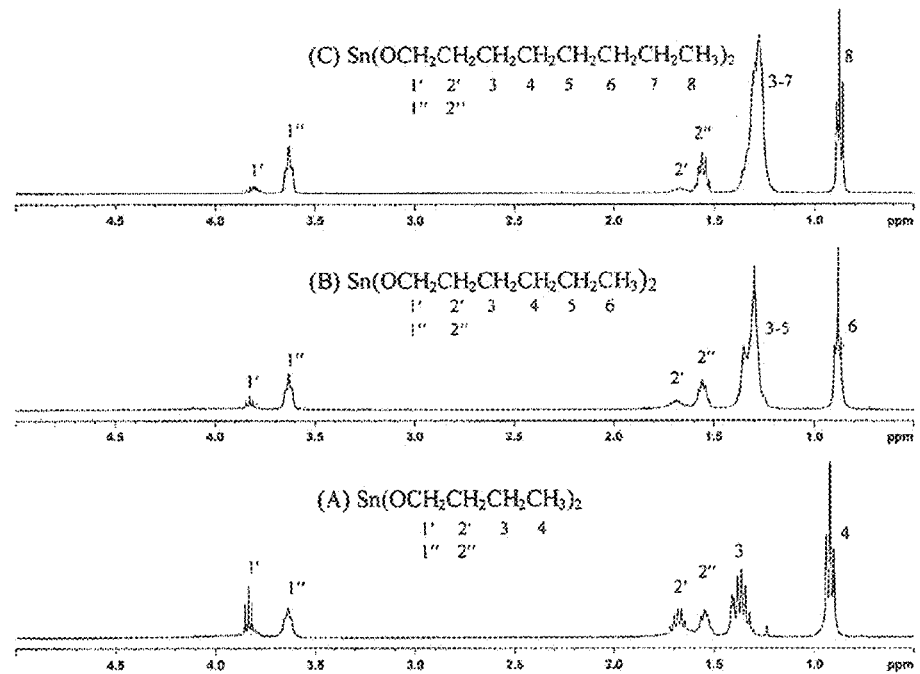
FIG. 3 shows the comparison of the $^1$H-NMR spectra (400 MHz, $CDCl_3$, 25° C.) of liquid tin(II) alkoxides: (A) tin(II) n-butoxide, (B) tin(II) n-hexoxide, and (C) tin(II) n-octoxide
Figure 4:
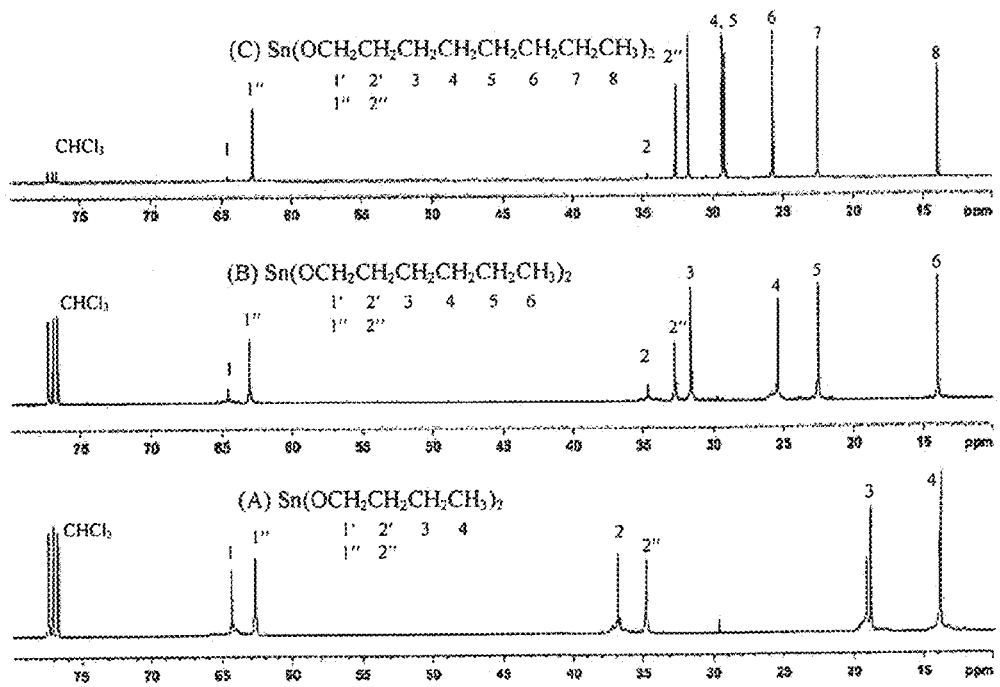
FIG. 4 shows the comparison of the $^{13}$C-NMR spectra (100 MHz, $CDCl_3$, 25° C.) of liquid tin(II) alkoxides: (A) tin(II) n-butoxide, (B) tin(II) n-hexoxide, and (C) tin(II) n-octoxide

Note:
[†] is molecular ion from GC-MS.
[‡] is molecular ion from LC-MS.
$^1$H-NMR characterization data are shown in FIG. 3 and Table 8, while the $^{13}$C-NMR characterization data are summarized in FIG. 4 and Table 9.

TABLE 8

$^1$H-NMR data of liquid tin(II) alkoxides (400 MHz, CDCl$_3$, 25° C.).

$Sn(OCH_2CH_2CH_2CH_3)_2$  $Sn(OCH_2CH_2CH_2CH_2CH_2CH_3)_2$  $Sn(OCH_2CH_2CH_2CH_2CH_2CH_2CH_2CH_3)_2$
1' 2' 3 4                1' 2' 3 4 5 6                        1' 2' 3 4 5 6 7 8
1" 2"                    1" 2"                                1" 2"

| | Chemical shift (δ, ppm) | | |
|---|---|---|---|
| Type of proton | $Sn(O-n-C_4H_9)_2$ | $Sn(O-n-C_6H_{13})_2$ | $Sn(O-n-C_8H_{17})_2$ |
| H-8 | — | — | 0.89 (t, J = 7.1 Hz) |
| H-7 | — | — |  |
| H-6 | — | 0.89 (t, J = 6.9 Hz) |  |
| H-5 | — |  | 1.18-1.41 (br m) |
| H-4 | 0.92 (t, J = 7.3 Hz) | 1.17-1.48 (br m) |  |
|  | 0.93 (t, J = 7.3 Hz) |  |  |
| H-3 | 1.27-1.47 (m) |  |  |
| H-2" | 1.48-1.60 (m) | 1.48-1.61 (m) | 1.50-1.61 (m) |
| H-2' | 1.60-1.74 (m) | 1.61-1.80 (br m) | 1.61-1.75 (m) |
| H-1" | 3.64 (br t) | 3.63 (br t, J = 6.2 Hz) | 3.63 (br t, J = 6.2 Hz) |
| H-1' | 3.80 (t, J = 6.7 Hz) | 3.80 (t, J = 6.7 Hz) | 3.80 (t, J = 6.7 Hz) |
|  | 3.87 (t, J = 7.1 Hz) | 3.83 (t, J = 7.1 Hz) | 3.83 (t, J = 7.1 Hz) |

Note:
t = triplet, m = multiplet, br = broad

TABLE 9

$^{13}$C-NMR data of liquid tin(II) alkoxides (100 MHz, CDCl$_3$, 25° C.).

$Sn(OCH_2CH_2CH_2CH_3)_2$  $Sn(OCH_2CH_2CH_2CH_2CH_2CH_3)_2$
1' 2' 3 4                1' 2' 3 4 5 6
1" 2"                    1" 2"
$Sn(OCH_2CH_2CH_2CH_2CH_2CH_2CH_2CH_3)_2$
1' 2' 3 4 5 6 7 8
1" 2"

| | Chemical shift (δ, ppm) | | |
|---|---|---|---|
| Type of carbon | $Sn(O-n-C_4H_9)_2$ | $Sn(O-n-C_6H_{13})_2$ | $Sn(O-n-C_8H_{17})_2$ |
| C-8 | — | — | 14.0 |
| C-7 | — | — | 22.6 |
| C-6 | — | 14.0 | 25.6 (w), 25.7 |
| C-5 | — | 22.6, 22.5 (w) | 29.2, 29.1 (w) |
| C-4 | 13.9, 13.8 | 25.6 (w), 25.4 | 29.4, 29.3 (w) |
| C-3 | 19.1, 18.9 | 31.6, 31.5 (w) | 31.8, 31.8 (w) |
| C-2',2" | 36.8, 34.8 | 34.7 (w), 32.8 | 34.7 (w), 32.7 |
| C-1',1" | 64.3, 62.7 | 64.6 (w), 63.1 | 64.5 (w), 62.8 |

Note:
w = weak

In conclusion, the synthetic process for producing liquid tin(II) n-butoxide, tin(II) n-hexoxide, and tin(II) n-octoxide can be successfully accomplished via the following important steps: 1) enough diethylamine in 2 or 3 mole equivalence of anhydrous tin(II) chloride to act as a base or ligand in the formation of SnCl$_2$.HNEt$_2$ in high yield, and 2) the use of nonpolar aprotic solvents such as n-heptane instead of alcohols such as methanol and ethanol. Molecules of n-heptane can solvate the tin(II) alkoxide, thereby preventing its self-aggregation during the reaction. Another important advantage of using nonpolar aprotic solvent systems is that they facilitate the precipitation and separation of the Et$_2$NH.HCl by-product from the soluble tin(II) alkoxide. Therefore, no further purification of the tin(II) alkoxide is required prior to its use as either a reagent or initiator. Finally, 3) the use of a suitable amount of alcohol of about 2-3 mole equivalence of the anhydrous tin(II) chloride can reduce the aggregation between the tin(II) alkoxide and the bridging alcohol. Tin(II) alkoxides produced from this process are viscous, dark yellow liquids, soluble in common organic solvents at room temperature, and can be stored for a long time under nitrogen or argon without any significant change in their reactivity. In addition, the products from the process can be used either as a reagent or an initiator without any extra purification and can be used either neat or in solution form.

The invention claimed is:

1. A process for producing a tin(II) alkoxide, comprising steps of:
adding one mole equivalent of anhydrous tin(ll) chloride to a reaction vessel;
adding 2 to 3 mole equivalents of an amine to the reaction vessel of the anhydrous tin(ll) chloride in a nonpolar, aprotic solvent;
further adding 2 to 3 mole equivalents of anhydrous alcohol ROH to the reaction vessel to provide a reaction mixture such that a newly produced tin(ll) alkoxide $Sn(OR)_2$ does not undergo self-aggregation;
stirring the reaction mixture for at least 3 hours in a temperature range of 25- 38° C. to provide a tin(ll) alkoxide $Sn(OR)_2$,
wherein the R group is selected from the group comprising $CH_3$, $C_2H_5$, $nC_3H_7$, $nC_4H_9$, $nC_5H_{11}$, $nC_6H_{13}$, $nC_7H_{15}$, and $nC_8H_{17}$ and the steps are carried out under inert atmosphere;
wherein the amine is selected from the group consisting of dimethylamine, diethylamine and diisopropylamine.

2. The process of claim 1, wherein the amine comprises diethylamine.

3. The process of claim 1, wherein the nonpolar, aprotic solvent is selected from the group consisting of n-heptane, n-hexane, cyclohexane, benzene, toluene, xylene, and tetrahydrofuran.

4. The process of claim 3, wherein the nonpolar, aprotic solvent comprises n-heptane.

5. The process of claim 1, wherein the nonpolar, aprotic solvent is dry n-heptane;
further comprising steps of:
adding dry n-heptane to the reaction vessel prior to addition of the anhydrous tin(II) chloride;
dissolving the anhydrous tin(II) chloride in the dry n-heptane;
maintaining a temperature range of 25-38° C. of the reaction mixture during addition of anhydrous alcohol ROH;
stirring the reaction mixture for about 12 hours;
filtering the reaction mixture to obtain a solid residue;
washing the solid residue with dry n-heptane;
evaporating a combined filtrate to dryness,
wherein the inert atmosphere is nitrogen or argon atmosphere.

6. A process for producing a tin(II) alkoxide, comprising steps of:
dissolving one mole equivalent of anhydrous tin(II) chloride in dry n-heptane in a reaction vessel in a temperature range of 25-38° C., wherein a resultant solution is stirred for 30-60 minutes;
adding 2 to 3 mole equivalents of diethylamine to the reaction vessel of the anhydrous tin(II) chloride in the temperature range of 15-20° C., wherein the resultant solution is stirred for 36 hours;
further adding 2 to 3 mole equivalents of anhydrous alcohol ROH to the reaction vessel to provide a reaction mixture such that a newly produced tin(II) alkoxide $Sn(OR)_2$ does not undergo self-aggregation;
stirring the reaction mixture for about 12 hours in a temperature range of 25-38° C.;
filtering the reaction mixture to obtain a solid residue;
washing the solid residue with dry n-heptane;
evaporating a combined filtrate to dryness to provide a tin(II) alkoxide $Sn(OR)_2$, wherein the R group is selected from the group comprising $nC_4H_9$, $nC_6H_{13}$, $nC_8H_{17}$ and the steps are carried out under nitrogen or argon atmosphere.

* * * * *